United States Patent [19]
Huszczuk et al.

[11] Patent Number: 5,165,278
[45] Date of Patent: Nov. 24, 1992

[54] CYCLE ERGOMETER

[75] Inventors: Andrew Huszczuk, Long Beach, Calif.; Steve Anderson, North Oakes, Minn.

[73] Assignee: Scientific Exercise Prescription, Inc., North Oakes, Minn.

[21] Appl. No.: 651,589

[22] Filed: Feb. 6, 1991

[51] Int. Cl.$^5$ .............................................. A61B 5/22
[52] U.S. Cl. .................................... 73/379; 482/900; 482/903
[58] Field of Search ............... 73/379, 862.17, 862.18; 272/73, DIG. 6; 482/900, 903, 6, 8, 57, 63

[56]  References Cited

U.S. PATENT DOCUMENTS

| | | | |
|---|---|---|---|
| 3,767,195 | 10/1973 | Dimick | 73/862.18 X |
| 4,244,021 | 1/1981 | Chiles, III | 73/379 X |
| 4,408,613 | 10/1983 | Relyea | |
| 4,463,764 | 8/1984 | Anderson et al. | |
| 4,647,036 | 3/1987 | Huszczuk | |
| 4,786,049 | 11/1988 | Lautenschlager | |
| 4,790,528 | 12/1988 | Nakao et al. | |
| 4,817,938 | 4/1989 | Nakao et al. | 272/73 |
| 4,934,692 | 6/1990 | Owens | |
| 4,934,694 | 6/1990 | McIntosh | |
| 4,941,652 | 7/1990 | Nagano et al. | 272/DIG. 6 X |
| 5,027,303 | 6/1991 | Witte | 73/862.36 X |

FOREIGN PATENT DOCUMENTS

| | | | |
|---|---|---|---|
| 0276125 | 7/1988 | European Pat. Off. | 482/903 |
| 8600024 | 1/1986 | World Int. Prop. O. | 482/903 |

OTHER PUBLICATIONS

"Computer Controlled Cycle Ergometer", Sherrill, Duane L. and George D. Swanson, IEEE Transactions on Biomedical Engineering, vol. BME-28, No. 10 (Oct. 1981).

"Dynamic troquemeter calibration of bicycle ergometers", Russell, J. C. and J. D. Dale, J. Appl. Physiol. 61(3):1217–1220, 1986.

*Primary Examiner*—Michael T. Razavi
*Assistant Examiner*—Elizabeth L. Shopbell
*Attorney, Agent, or Firm*—Haugen and Nikolai

[57]  ABSTRACT

An improved bicycle ergometer system is disclosed which reduces the limitation on the work input necessary to operate the device and, at the same time, accomplishes an increase in the relative amount of isotonic exercise provided by operation of the system. The system provides real-time auxiliary energy input control based on the instantaneous difference between the actual operator work rate and the intended work rate. The preferred embodiment includes a stationary bicycle frame having a pedal and crank assembly mechanically coupled to an output shaft. A clutch-connected, double-ended electric motor can be used to provide the rotational torque necessary to bring the output shaft up to a desired speed, if desired, prior to the onset of a physical output test. It can also control the intended work rate to a level of zero operator work rate input. In one embodiment, a flywheel is also mounted on the motor output shaft. The flywheel manually operates in conjuction with an electromagnetic magnet/coil eddy current braking system to apply a retarding force to the driveshaft of the bicycle ergometer on a time-variable basis.

23 Claims, 4 Drawing Sheets

CYCLE ERGOMETER

BACKGROUND OF THE INVENTION

I. Field of the Invention

The present invention relates generally to exercise equipment including systems and devices for measuring the energy output of a person during specific exercise to aid in evaluating the physical condition of the individual. More specifically, the invention is directed to a stationary bicycle ergometer system which measures the energy expended by the operator of a pedal cranking system in which both additional rotational torque and resistance to rotational torque or braking force can be externally applied to the system by separate auxiliary devices. The system eliminates the need for a massive flywheel and the applied force on the pedal and crank assembly required to initially overcome the inertia of the flywheel and subsequently maintain its rotation. Instantaneous rotational speed of pedalling and angular position of the pedal and crank assembly are accurately measured by relatively simple and sensitive analog devices to provide accurate input for energy measurement and device control in order to minimize the isometric component of exercise.

II. Description of the Related Art

Bicycle ergometers have been widely used to impose defined levels of physical work on human subjects. This has been done both for purposes of research in exercise physiology and for diagnostic purposes with regard to exercise, stress testing, or the like. In one common type of such device, the work produced by the operator in manually maintaining rotation of a flywheel by driving the pedal and crank system of a stationary bicycle is measured against resistance produced by applying a known braking force to the flywheel.

Many of the patients that are tested on devices of the class described have chronic cardiac problems or are otherwise weak or infirm and, for this reason, one of the desirable goals of such devices is to reduce the minimum work input required to operate the bicycle ergometer prior to a deliberate application of a retarding force, i.e., the onset of a test. One prior solution to this problem involved the use of an auxiliary motor to overcome the inertia in the flywheel from rest to a selected speed of rotation and thereafter allowing the user to expend energy only in maintaining the operation of the bicycle ergometer against a specific known applied braking force or, in some cases, no applied force at all. An example of such a device is illustrated and described in U.S. Pat. No. 4,647,036 to A. Huszczuk, a co-inventor in the present application. That device does not, however, provide means to actually measure the work output generated.

In addition, the operation of such devices heretofore contrived by the very nature of the pedal crank involves the expending of a great deal of the user's energy by the way of an isometric component of exercise. This, of course, involves muscular contraction or changing muscle tension with the ends of the muscle staying relatively fixed in place. In other words, significant changes in tension may occur without appreciable compensating changes in muscle length. From the standpoint of the measurement of the user's or patient's physical condition or with respect to benefitting the patient's or user's health, isometric exercise is not as desirable as isotonic exercise. In isotonic exercise, the muscle tension or force exerted is kept relatively constant with respect to the length of the muscle. As force is increased, the muscle is allowed to stretch, for example. It would be a distinct advantage if such a device were to reduce the relative amount of isometric effort.

Thus, those working with devices of the bicycle ergometer type have long sought to reduce the lower limit on the work effort for a user so that the weakest and most infirm patients can be monitored and helped. It is an additional goal of the evolution of such machines to increase the relative amount of isotonic work associated with the use of the device relative to the amount of isometric, i.e., unproductive energy expenditure, so that the operation of the device is more beneficial to the user. In addition, simplification of such devices both mechanically and electrically would be beneficial.

Accordingly, it is a principal object of the present invention to provide a bicycle ergometer having the ability to reduce the relative amount of isometric muscular effort required to operate the device.

Another object of the present invention is to reduce the minimum energy required to effect operation of the bicycle ergometer.

A still further object of the present invention is to enable the direct measurement of work output produced by the user of such a device.

A still further object of the present invention is to devise a bicycle ergometer which has the ability to modulate braking torque on a real time basis in accordance with the sensed rotational torque, position and speed of the pedal and crank assembly in a closed loop feedback system to optimally perform work at any preset level regardless of the pedalling cadence.

SUMMARY OF THE INVENTION

By means of the present invention, there is provided an improved bicycle ergometer system which reduces the limitation on the work input necessary to operate the device and, at the same time, accomplishes an increase in the relative amount of isotonic exercise performed by operation of the system. This is accomplished by a relatively simplified but sophisticated device.

The preferred embodiment includes a stationary bicycle frame having a pedal and crank assembly journaled for rotation in the frame together with one-way (freewheeling) clutch and a gear system which couples the crank to a double-ended driveshaft of an electric motor. The electric motor is provided to generate the rotational torque necessary to bring the output shaft up to a desired speed prior to the onset of a physical output test. This is especially useful in the case of a weak or infirm user who would have to expend too much energy to overcome the original system inertia and mechanical friction to bring the device up to speed and maintain it on his own. a relatively light conductive flywheel is provided and mounted on one end of the driveshaft. In this manner, both the flywheel and the pedal and crank assembly are connected to the driveshaft of a motor, the pedal crank through the one-way clutch and a speed multiplying gearing system. The flywheel operates in conjunction with an electromagnetic core/coil eddy current braking system to apply a retarding force to the driveshaft as desired. The flywheel is preferably copper and can be relatively light weight in comparison to traditional, relatively massive, high inertia flywheels used on such devices.

A strain gauge is mounted between the bicycle frame and the drive train system assembly in a manner such that it prevents rotation of that assembly while a force is applied to pedals and whereby it actually senses the rotational component of a force applied to the pedal and crank assembly throughout the entire rotational cycle. The strain gauge transduces the mechanical force applied and generates a real time analog electrical signal proportional to the instantaneous force being sensed. An additional measuring transducer device in the form of a hollow shaft pancake resolver is mounted on the crankshaft in the space between the gear system and one of two mounting brackets on which, by means of ball bearings, or the like, the entire drive train system assembly is rotatably carried. The resolver produces an analog electrical signal related to the instantaneous angular position of the pedal and crank assembly and thereby a signal related to the instantaneous speed of rotation of the pedal and crank assembly can be derived. Calculation means is provided for determining the work output based on the rotational component of the force applied to the pedal and crank assembly and the speed of rotation of the pedal and crank assembly. The work output, of course, an be compared to any desired target or goal work output.

The resolver system, in the preferred embodiment, further takes advantage of the known relationship between the directional vectors of the force applied by the operator of the pedal and crank assembly relative to the angular position of each pedal throughout the revolution cycle. This known relationship can be utilized to control the electromagnetic braking force in a real time manner such that the muscular effort required to be expended for any given task by each of the legs of the user with respect to the corresponding pedal is reduced to a great degree for each leg stroke throughout the 360-degree revolution or cranking cycle thereby maximizing the relative contribution of isotonic exercise and work.

BRIEF DESCRIPTION OF THE DRAWINGS

In the drawings, wherein like numerals are utilized to designate like parts throughout the same.

DETAILED DESCRIPTION

Figure 1:
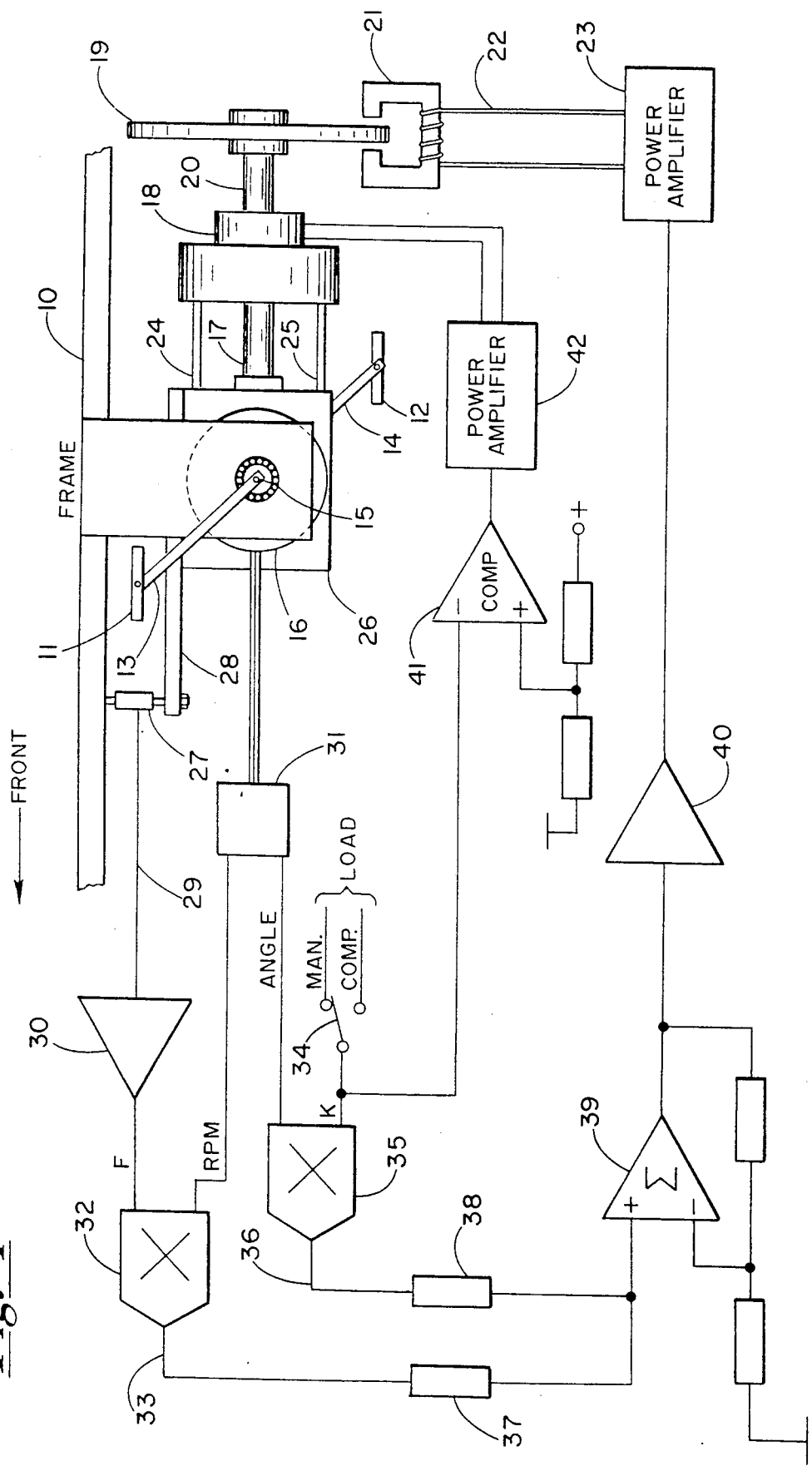
FIG. 1 is a schematic block diagram illustrating the components of one embodiment of the bicycle ergometer of the invention.

One embodiment of the cycle ergometer system of the invention is depicted by the schematic block diagram of FIG. 1. The system includes a bicycle frame generally represented by 10 having a pedal-powered cranking system including pedals 11 and 12 connected respectively to crank arms 13 and 14 which are suitably mounted on crankshaft 15 which, in turn, is rotatably journaled in the bicycle frame for foot powered rotation together with the rotor of a pancake resolver at 16. The crankshaft 15, in turn, is suitably adapted to form a part of a one-way clutch (not shown) engaging a gear system. Suitable gears mechanically increase the rotational speed at a ratio of about 30:1 in a well-known manner and, in turn, connect the crank assembly to a shaft 17 of an electric motor 18. A relatively light conductive flywheel is illustrated at 19 mounted on a shaft 20 which is coextensively connected to the motor shaft 17 as by the utilization of a double-ended motor shaft, or the like. The flywheel disc 19 is made out of an electrically conducting material, preferably copper, and is disposed to cooperate with an eddy current braking system consisting of a core 21 and conductive coil 22 energized by a power amplifier as at 23.

Suitable structural members are also provided in the system as illustrated at 24 and 25 to structurally integrate the 17-18-19-20 assembly with a clutch-gear housing 26. The frame 10 is further provided with a strain gauge mechanism 27 connected between the upper frame of the cycle ergometer and a gear-clutch housing extension plate 28 in a manner which allows precise measurement of the rotational component of the force applied to the pedals II and 12 by the operator of the cycle ergometer. The strain gauge 27, of course, produces an electrical signal which is proportional to the force sensed. The signal is conducted via conductor 29 to a calibration amplifier 30 which produces a calibrated force output F.

The resolver 16, as is well known, has the ability to sense the instantaneous rotational position of the crank assembly on a continuous basis and hence the instantaneous rotational speed of the pedal and crank assembly. The resolver is electrically coupled to a calculating device which may be a microprocessor resolver to DC converter 31 which generates corresponding outputs with regard to the instantaneous speed (rpm) of the device together with the instantaneous rotational angle of the device.

The instantaneous speed together with the output force from the strain gauge are fed to a calculation device, which may be a conventional multiplying device 32, which, in turn, produces an output 33 indicative of the instantaneous value of the work being produced by the operator of the cycle ergometer. A manual/computerized switch 34 can be utilized to implement automated or manual control of the load applied by the power amplifier 23 to the dynamic braking system of the eddy current brake as desired. This is achieved by a further multiplying system 35 utilized to modulate the level of angle signal by a scaling factor K, manually or computer adjusted, typically between 0 and 1, i.e., 0 and 100%, range of a braking force. The resulting output 36 constitutes a driving signal which modulates the instantaneous braking force applied to the flywheel 19 in a manner closely resembling that illustrated in FIGS. 4 and 5. The negative feedback loop is completed by summation of the opposite polarity output signals 33 and 36 by means of respective resistors 37 and 38 and a summing amplifier 39. The resulting error signal, i.e., the difference between the intended signal at the output 36 and the actually generated work output signal at 33, determines, via buffer amplifier 40 and a power amplifier 23, the instantaneous amount of electric current fed into coil 22. In addition, for the intended 0 or a very low values of K, a comparator 41 is preset to switch a power amplifier 42 into a mode of operation that energizes an electric motor 18 to maintain rotation of a gear-motor-flywheel assembly in order to overcome initial inertial and frictional energy requirements to enable real 0 Watt work setting as well as a precise work load control within the initial work range which may be a 0 to 20 watt work range.

Figure 2:
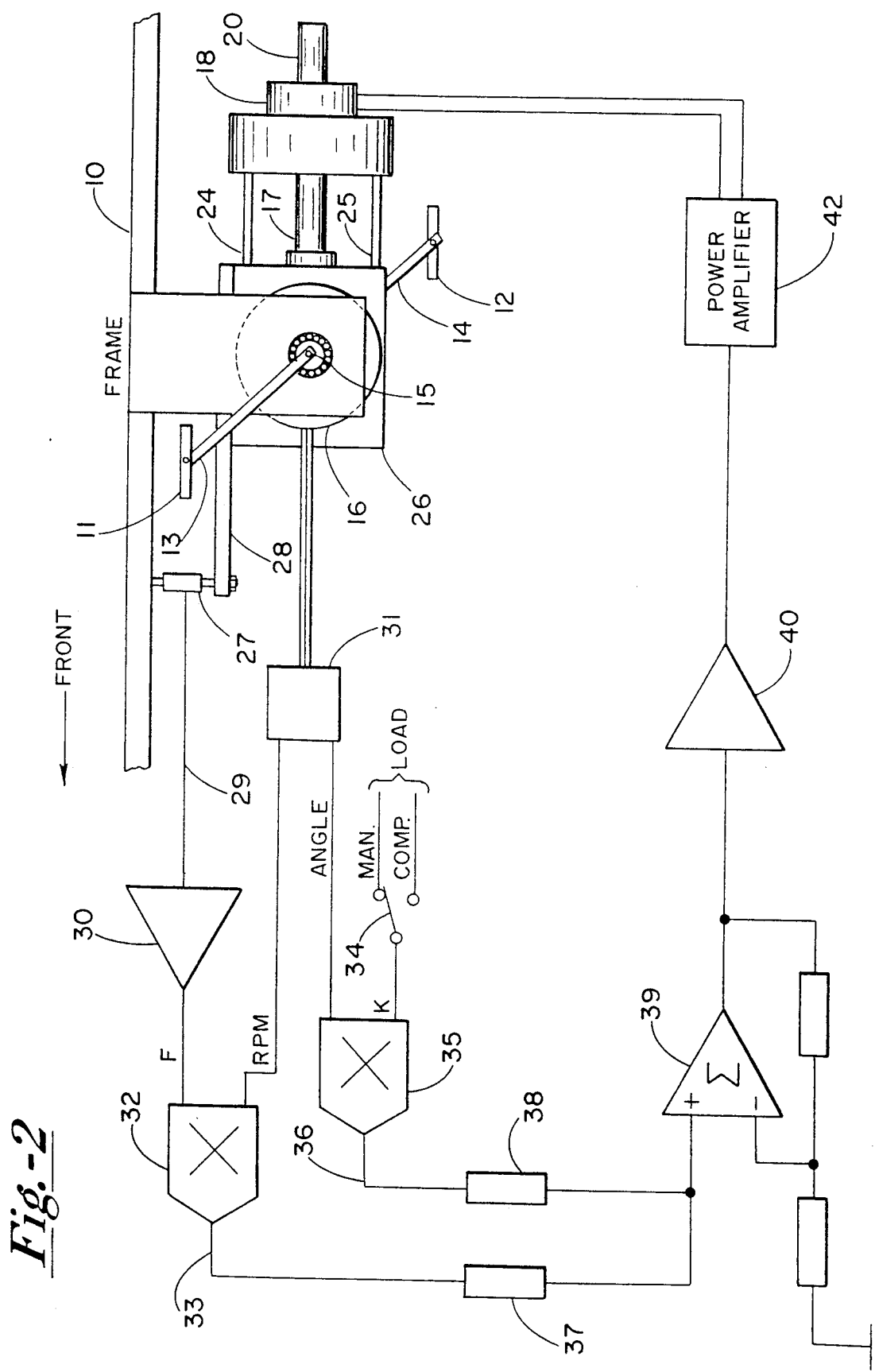
FIG. 2 is a schematic block diagram illustrating an alternate embodiment to that of FIG. 1.

FIG. 2 represents an alternate, simplified version of the cycle ergometer system of FIG. 1 in which the flywheel and associated eddy current brake system are not used. Instead, the operation of the device is controlled entirely by feeding the error signal at the output of the summing amplifier 39 via buffer amplifier 40 into the power amplifier 42, thus enabling control of the polarity and amount of electric current energizing the electric motor 18, thereby, depending on the load setting, the motor will assist or resist the pedalling effort of the operator. The elimination of the flywheel and associated braking or resistance force applying system does not present a drawback in applications where low to moderate maximal work limits will suffice to accommodate patient operators. This system allows a very low to moderate work setting to be used without the necessity of using a more powerful electric motor and a means of forced cooling to dissipate the heat generated by the motor during braking.

Figure 3:
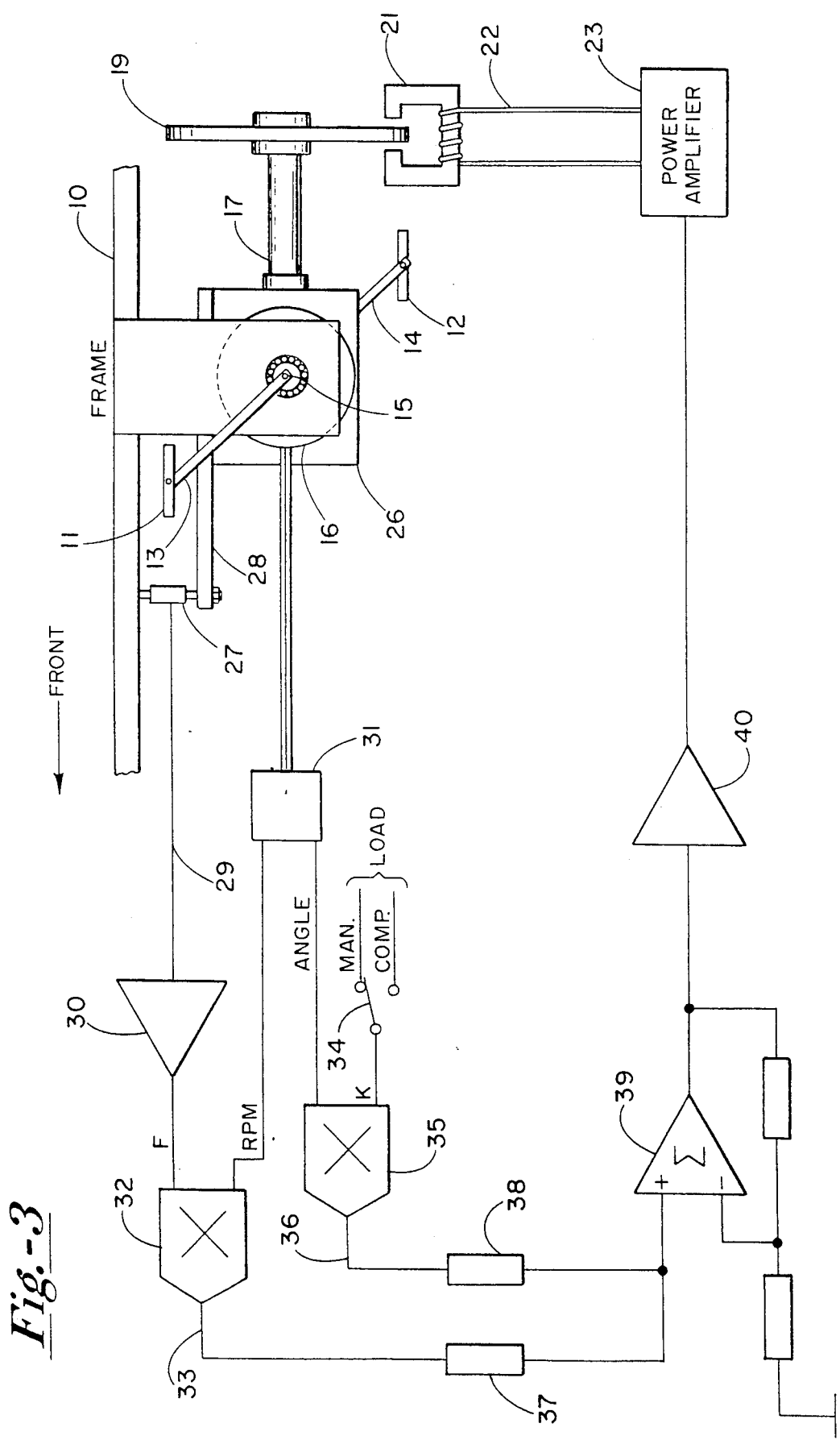
FIG. 3 is a schematic block diagram of another alternate embodiment of the bicycle ergometer of the invention.

FIG. 3 represents another alternative embodiment of the cycle ergometer system of the invention in the form of a manually operated version of the system of FIG. 1. In this system, the motor or power assist function has been eliminated, leaving a completely manually operated ergocycle with unaided start-up. This embodiment is especially useful in rehabilitation and training situations to allow desired exertion by the operator beyond very low load settings.

Figure 4:
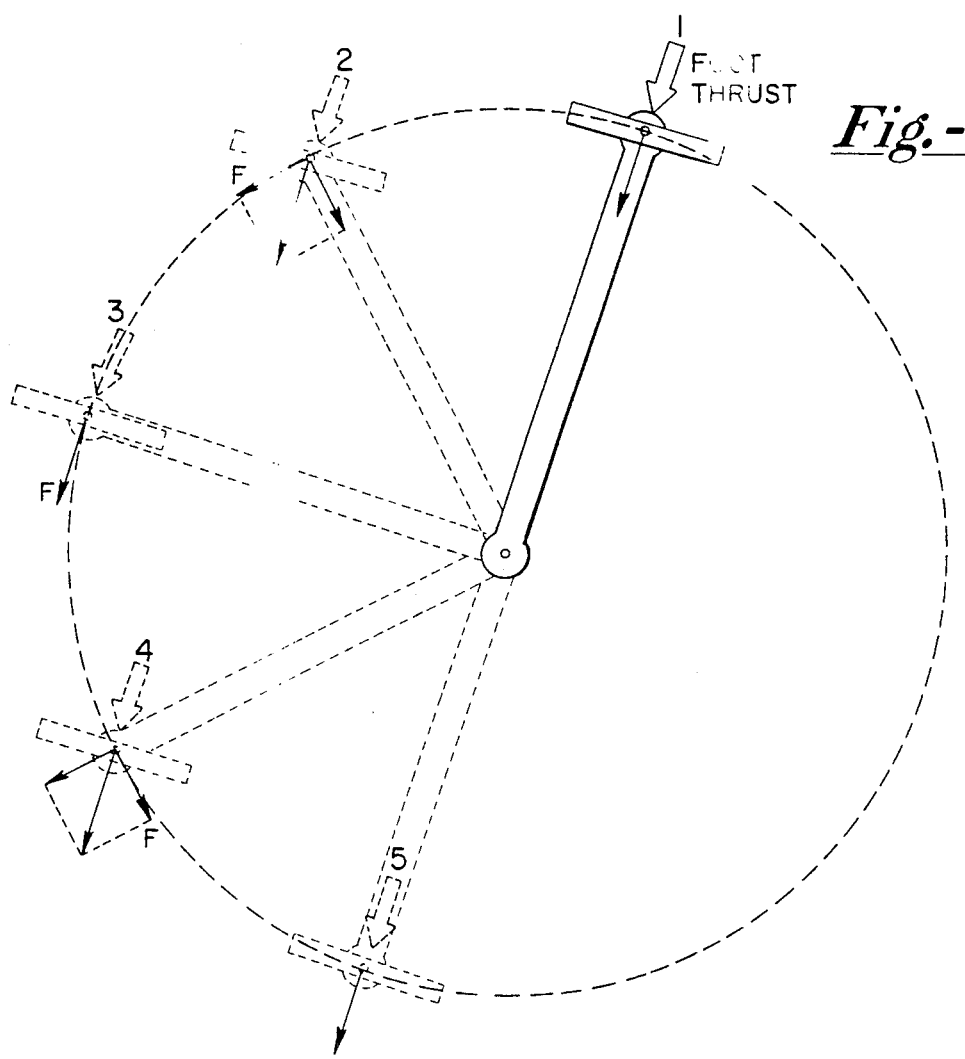
FIG. 4 is an illustration showing multiple position force vector diagrams of the rotational and the crank arm squeezing/stretching force components of a foot thrust versus position with respect to one pedal of a pedal and crank assembly.
Figure 5:
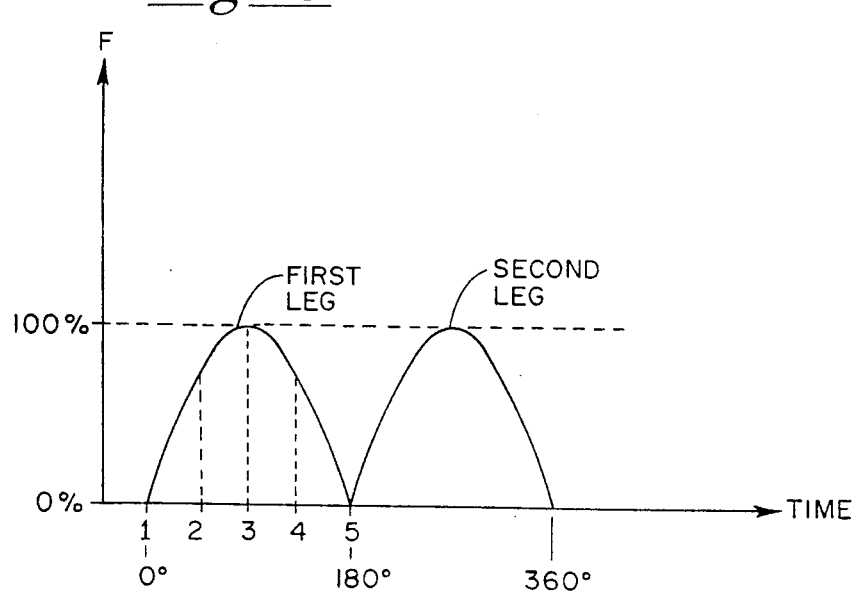
FIG. 5 is a graphical illustration of the relative rotational sustaining force of FIG. 4 in the five position with respect to both pedals during a 360-degree revolution of the crank assembly.

The rotation position versus torque output relation is illustrated in FIGS. 4 and 5. As noted in those figures, the maximum useful foot thrust occurs when the force of the foot is tangential to the rotational trajectory as illustrated by position 3 in the Figures. Thus, at positions 1 and 5 (1 corresponding to the top dead center and 5 to the bottom of the stroke), the actual force which is being utilized for rotation sustaining is zero at the extremes and it varies between that and 100% at the longitudinal position 3 during each half revolution which corresponds to the push stroke of each of the two legs.

The diagram of FIG. 5 further illustrates this phenomenon in the form of the force signal F which corresponds to the output of calibration amplifier 30 in FIGS. 1, 2 and 3. It is quite important to note that in typical existing cycle ergometers, the useful rotation sustaining force component of a foot thrust, although not measured, is undergoing these identical fluctuations during every cycle. Yet the opposing braking force is applied at a constant or 100% level. The difference between this steady force level and the useful modulating foot force profile represents predominantly wasted muscular energy, i.e., the isometric exercise. By varying the amount of braking action, according to sensed crank position, on a real time basis in the likeness of the force signal F, the above-mentioned difference can be greatly reduced. This, in turn, increases the relative amount of isotonic exercise produced relative to the total amount of effort expended.

This invention has been described herein in considerable detail in order to comply with the Patent Statutes and to provide those skilled in the art with the information needed to apply the novel principles and to construct and use such specialized components as are required. However, it is to be understood that the invention can be carried out by modified or specifically different equipment and devices, and that variations and modifications, both as to equipment details and operating procedures, can be accomplished without departing from the scope of this invention itself.

What is claimed is:

1. An exercise apparatus that controls the rotational operation of a rotatable mass based on the on-going, real-time value of a reference work rate and an ongoing, real-time measurement of a work rate developed by an operator in manually maintaining rotational operation of the rotatable mass comprising:

means for rotatably mounting the rotatable mass;

rotating manual drive input means for enabling an operator to apply force through a distance to manually maintain rotation of the rotatable mass;

retarding means for applying resistive force to retard the rotation of the rotatable mass on a time variable basis;

operator work rate input determining means further including;

force measuring means for sensing an instantaneous rotational component of a force applied by the operator to the rotating manually drive input means and generating a first electrical signal related to the force being sensed, transducer means for producing a second electrical signal indicative of an instantaneous rotational speed of the force applied by the operator;

means for determining an instantaneous value of the operator work rate input based on the instantaneous force applied by the operator and the instantaneous speed of the applied force and generating an operator work rate electrical signal indicative of the instantaneous value of the operator work rate input;

reference work rate input determining means further including;

transducer means for producing a third electrical signal indicative of an instantaneous angular position of the rotating manual drive input means, means for determining a corresponding instantaneous value of the reference work rate input based on the third electrical signal and generating a reference work rate electrical signal indicative of the instantaneous value of the reference work rate input;

means for comparing the value of the operator work rate and reference work rate electrical signals, determining the difference therebetween, and generating a time-variable electrical error signal indicative of that difference; and means for controlling the retarding means based on the electrical error signal.

2. The apparatus of claim 1 wherein the manual drive input means is a pedal operated crank and the rotatable mass is a flywheel.

3. The apparatus of claim 2 wherein the retarding means is an eddy current brake.

4. The apparatus of claim 3 including means to vary an amount of current supplied to the eddy current brake on a continual time-varying basis based on the error signal value.

5. The apparatus of claim 4 wherein the means to vary the amount of current supplied to the eddy current brake for controlling the retarding means comprises a buffer amplifier and a variable power amplifier.

6. The system of claim 1 wherein the manual drive input means is a pedal-operated crank assembly and the transducer means for producing the second and third electrical signals relating to the instantaneous speed and angular position of the crank assembly is an analog resolver.

7. An exercise apparatus which controls the rotational operation of a rotatable mass based on the on-going, real-time value of a reference work rate and an on-going, real-time measurement of a work rate developed by an operator in manually maintaining rotational operation of a rotatable mass comprising:

means for rotatably mounting the rotatable mass;
  rotating manual drive input means for enabling an operator to applying force through a distance to manually maintain rotation of the rotatable mass;
  electric motor means for overcoming inertia and having an output connected to rotate the rotatable mass in cooperation with the manual drive input;
  retarding means for applying resistive force to retard the rotation of the rotatable mass on a time variable basis;
  operator work rate input determining means further including;
    force measuring means for sensing an instantaneous rotational component of a force applied by the operator to the rotating manual drive input means and generating a first electrical signal related to the force being sensed,
    transducer means for producing a second electrical signal indicative of an instantaneous rotational speed of the force applied by the operator;
    means for determining instantaneous value of the operator work rate input based on the force applied by the operator and the speed of the applied force and generating an operator work rate electrical signal indicative of the instantaneous value of the operator work rate input;
  reference work rate input or set point determining means, further including;
    transducer means for producing a third electrical signal indicative of the instantaneous angular position of the rotating manual drive input means,
    means for determining a corresponding instantaneous value of the reference work rate input and generating a reference work rate electrical signal indicative of the instantaneous value of the reference work rate input;
  means for comparing the value of the operator work rate/reference work rate electrical signals, determining the difference therebetween, and generating a time-variable electrical error signal indicative of that difference;
  means for continuously controlling the retarding means based on the electrical error signal; and
  means for controlling the operation of the electric motor means.

8. The apparatus of claim 7 wherein the means for controlling the motor means comprises:
  means for sensing a value indicative of the intended work rate; and
  means to energize and modulate power input to the electric motor to maintain rotation of the rotatable mass in a manner that allows control of the reference work rate at a level below that required to overcome initial inertial and/or on-going frictional energy dissipation in the apparatus.

9. The apparatus of claim 7 wherein the rotating manual drive input means is a pedal operated crank assembly and the rotatable mass in a flywheel.

10. The apparatus of claim 9 wherein:
  the retarding means is an eddy current brake;
  the means for controlling the retarding means included means for modulating the amount of current applied to the eddy current brake on a continual time-variable basis based on the error signal value.

11. The system of claim 10 wherein the transducer means for producing the second and third electrical signals relating to the instantaneous speed and angular position of the pedal operated crank assembly is an analog resolver.

12. The apparatus of claim 8 wherein the manual drive input means is a pedal-operated crank assembly.

13. The apparatus of claim 8:
  wherein the means for sensing the value indicative of the reference work rate includes transducer means which generates a fifth electrical signal indicative of the reference work rate;
  wherein the apparatus further comprises comparator means for comparing the value of the fifth electrical signal with a predetermined electrical signal indicative of frictional energy dissipation in the apparatus or other inherent energy loss to be overcome and generating a sixth electrical signal indicative of the difference between the reference work rate and frictional energy dissipation or other inherent energy loss to be overcome; and
  wherein the means for controlling the operation of the motor means includes means for utilizing the sixth electrical signal to control power input to the electric motor.

14. The apparatus of claim 13 wherein the rotating manual drive input is a pedal operated crank assembly.

15. The apparatus of claim 13 wherein the means utilizing the fifth electrical signal comprises a variable power amplifier.

16. The system of claim 14 wherein the transducer means for producing the second and third electrical signals relating to the instantaneous speed and angular position of the pedal operated crank assembly is an analog resolver.

17. An exercise apparatus which controls the rotational operation of a rotatable mass based on the on-going, real-time measurement of a work rate developed by an operator in manually maintaining rotational operation of a rotatable mass comprising:
  means for rotatably mounting the rotatable mass;
  rotating manual drive input means for enabling an operator to apply force through a distance to manually maintain rotation of the rotatable mass;
  electrical motor means for overcoming inertia and having an output connected to rotate the rotatable mass in cooperation with the manual drive input;
  operator work rate input determining means further including;
    force measuring means for sensing an instantaneous rotational component of a force applied by the operator to the rotating manual drive input means and generating a first electrical signal related to the force being sensed, transducer means for producing a second electrical signal indicative of an instantaneous rotational speed of the force applied by the operator;

means for determining instantaneous value of the operator work rate input based on the force applied by the operator and the speed of the applied force and generating an operator work rate electrical signal indicative of the instantaneous value of the operator work rate input;

reference work rate input determining means, further including;

transducer mean for producing a third electrical signal indicative of the instantaneous angular position of the rotating manual drive input means, means for determining a corresponding instantaneous value of the reference work rate input based on the third electrical signal and generating a reference work rate electrical signal indicative of the instantaneous value of the reference work rate input;

means for comparing the value of the operator work rate/reference work rate and electrical signals, determining the difference therebetween, and generating a time-variable electrical error signal indicative of that difference;

means for controlling the operation of the motor means comprising;

means for sensing a value indicative of the reference work rate and;

means to energize and modulate power input to the electric motor to maintain rotation of the rotatable mass in a manner that allows control of the reference work rate at a level below that required to overcome initial inertial and/or ongoing frictional energy dissipation in the apparatus.

18. The apparatus of claim 17:

wherein the means for sensing the value indicative of the reference work rate includes transducer means which generates a fifth electrical signal indicative of the reference work rate;

wherein the apparatus further comprises comparator means for comparing the value of the fifth electrical signal with a predetermined electrical signal indicative of frictional energy dissipation in the apparatus or other inherent energy loss to be overcome and generating a sixth electrical signal indicative of the difference between the reference work rate and frictional energy dissipation or other inherent energy loss to be overcome; and wherein the means for controlling the operation of the motor means includes means for utilizing the sixth electrical signal to control power input to the electric motor.

19. The apparatus of claim 18 wherein the rotating manual drive input is a pedal operated crank assembly.

20. The system of claim 19 wherein the transducer for producing the second and third electrical signals relating to the instantaneous speed and angular position of the pedal operated crank assembly is an analog resolver.

21. The apparatus of claim 17 wherein the power input to the motor is controlled on a time-variable basis in accordance with the electrical error signal.

22. A method of operating an exercise apparatus that controls the rotational operation of a rotatable mass based on the on-going, real-time measurement of a work rate developed by an operator in manually maintaining rotational operation of the rotatable mass comprising the steps of:

providing a means for rotatably mounting the rotatable mass;

providing a rotating manual drive input means for enabling an operator to apply force through a distance to manually maintain rotation of the rotatable mass;

providing a retarding means for applying resistive force to retard the rotation of the rotatable mass on a time-variable basis;

determining the operator work rate input by sensing an instantaneous rotational component of a force applied by the operator to the rotating manual drive input means, sensing the instantaneous rotational speed of the force applied by the operator and determining the instantaneous value of the operator work input based on the force applied by the operator and the speed of the applied force;

generating an operator work rate electrical output signal indicative of the instantaneous value of the operator work rate input;

determining the instantaneous reference work rate input by measuring the instantaneous angular position of the rotating manual input drive means and based thereon generating a time-variable reference work rate electrical signal indicative of the instantaneous value of the reference work rate input;

comparing the value of the operator work rate and reference work rate and generating a time-variable electrical error signal indicative of the difference therebetween; and controlling the operation of the retarding means based on the error signal generated.

23. A method of operating an exercise apparatus that control the rotational operation of a rotatable mass based on the on-going, real-time measurement of a work rate developed by an operator in manually maintaining rotational operation of the rotatable mass and an reference work rate comprising the steps of:

providing a means for rotatably mounting the rotatable mass;

providing a rotating manual drive input means for enabling an operator to apply force through a distance to manually maintain rotation of the rotatable mass;

providing an electric motor for overcoming inertia and frictional resistance having an output connected to rotate the rotatable mass in cooperation with the manual drive input on a time-variable basis;

providing means for generating an electrical signal indicative of an instantaneous reference work rate;

providing means for generating an electrical signal indicative of an instantaneous value of a frictional or other total energy dissipation to be overcome;

determining the operator work rate input by sensing an instantaneous rotational component of a force applied by the operator to the rotating manual drive input means, sensing the instantaneous rotational speed of the force applied by the operator and determining the instantaneous value of the operator work input based on the force applied by the operator and the speed of the applied force;

generating an operator work rate electrical output signal indicative of the instantaneous value of the operator work rate input;

determining the instantaneous reference work rate input by measuring the instantaneous angular position of the rotating manual input drive means and based thereon generating a time-variable reference work rate electrical signal indicative of the instantaneous value of the reference work rate input;

generating a time-variable electrical signal indicative of the instantaneous frictional energy dissipation;

comparing the value of the reference work rate signal and the frictional energy dissipation signal and generating a signal indicative of the difference therebetween; and controlling the electric motor to provide an input required to reduce the reference energy dissipation needed to be overcome by the operator to the work rate level.

* * * * *

UNITED STATES PATENT AND TRADEMARK OFFICE
CERTIFICATE OF CORRECTION

PATENT NO. : 5 165 278

DATED : November 24, 1992

INVENTOR(S) : Andrew Huszczuk et al

It is certified that error appears in the above-identified patent and that said Letters Patent is hereby corrected as shown below:

In column 6, line 27, delete "manually" and insert -- manual --.

In column 6, line 52, the subparagraph should be a single indented subparagraph rather than a double indented subparagraph In column 6, line 57, the subparagraph should be a single indented subparagraph rather than a double indented subparagraph.

In column 8, line 59, delete "electrical" and insert -- electric --.

In column 8, line 64, the subparagraph should be a double indented subparagraph rather than a single indented subparagraph.

In column 9, line 4, the subparagraph should be a double indented subparagraph rather than a single indented subparagraph.

In column 6, line 12, the subparagraph should be a double indented subparagraph rather than a single indented subparagraph.

UNITED STATES PATENT AND TRADEMARK OFFICE
CERTIFICATE OF CORRECTION

PATENT NO. : 5,165,278

DATED : November 24, 1992

INVENTOR(S) : Andrew Huszczuk et al

It is certified that error appears in the above-indentified patent and that said Letters Patent is hereby corrected as shown below:

In column 9, line 12, delete "mean" and insert --means--.

In column 10, line 36, delete "control" and insert --controls--.

Signed and Sealed this

Nineteenth Day of October, 1993

Attest:

BRUCE LEHMAN

Attesting Officer

Commissioner of Patents and Trademarks